United States Patent
Kappler

(10) Patent No.: US 8,628,241 B2
(45) Date of Patent: Jan. 14, 2014

(54) METHOD FOR CALIBRATING A CT SYSTEM WITH AT LEAST ONE FOCUS-DETECTOR COMBINATION WITH A QUANTA-COUNTING DETECTOR

(75) Inventor: Steffen Kappler, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 60 days.

(21) Appl. No.: 13/271,443

(22) Filed: Oct. 12, 2011

(65) Prior Publication Data
US 2012/0093282 A1    Apr. 19, 2012

(30) Foreign Application Priority Data
Oct. 13, 2010   (DE) .......................... 10 2010 042 388

(51) Int. Cl.
G01D 18/00 (2006.01)
A61B 6/00 (2006.01)

(52) U.S. Cl.
USPC .................. 378/207; 378/5; 378/18; 382/131

(58) Field of Classification Search
USPC ............................ 378/5, 9, 18; 382/130, 131
See application file for complete search history.

(56) References Cited

U.S. PATENT DOCUMENTS

| | | | | |
|---|---|---|---|---|
| 4,225,789 A | * | 9/1980 | Albrecht ............................ | 378/5 |
| 4,352,020 A | * | 9/1982 | Horiba et al. .................... | 378/18 |
| 5,214,578 A | * | 5/1993 | Cornuejols et al. ............ | 378/207 |
| 5,473,656 A | * | 12/1995 | Hsieh et al. ....................... | 378/4 |
| 5,473,663 A | * | 12/1995 | Hsieh .............................. | 378/207 |
| 5,734,691 A | * | 3/1998 | Hu et al. ............................ | 378/4 |
| 5,774,519 A | * | 6/1998 | Lindstrom et al. .............. | 378/18 |
| 5,822,393 A | * | 10/1998 | Popescu ........................ | 378/108 |
| 7,922,390 B2 | * | 4/2011 | Holt et al. ...................... | 378/207 |
| 8,315,352 B2 | * | 11/2012 | Wu et al. ........................... | 378/5 |
| 2003/0142857 A1 | * | 7/2003 | Alyassin ........................ | 382/131 |
| 2004/0022364 A1 | * | 2/2004 | Stierstorfer et al. .......... | 378/207 |

(Continued)

FOREIGN PATENT DOCUMENTS

| DE | 10224315 A1 | 12/2003 |
|---|---|---|
| DE | 102004062857 A1 | 7/2006 |
| DE | 102006025401 A1 | 12/2007 |

OTHER PUBLICATIONS

German Office Action for German Patent Application No. DE 10 2010 042 388.2 dated Jul. 6, 2011.

(Continued)

*Primary Examiner* — Alexander H Taningco
(74) *Attorney, Agent, or Firm* — Harness, Dickey & Pierce, P.L.C.

(57) ABSTRACT

A method is disclosed for calibrating a CT system with at least one focus-detector combination with a quanta-counting detector including a plurality of detector elements, with the focus-detector combination being arranged to enable it to be rotated around a measurement region and a system axis arranged therein, and an X-ray bundle going out from the focus to the detector which possesses an X-ray energy spectrum over an energy range. In at least one embodiment of the method, actual attenuation values from CT scans obtained with an X-ray energy spectrum are compared with theoretical mono-energetic required attenuation values even in the paralysis range of the quanta-counting detector and a transfer function is determined between the required attenuation values and the actual attenuation values for each detector element and thereby a calibration of the measured attenuation values is carried out.

24 Claims, 4 Drawing Sheets

(56) References Cited

U.S. PATENT DOCUMENTS

2004/0228451 A1* 11/2004 Wu et al. .................. 378/207
2005/0259784 A1* 11/2005 Wu et al. .................... 378/19
2006/0109950 A1* 5/2006 Arenson et al. ................ 378/4
2006/0146984 A1 7/2006 Bruder et al.
2008/0001093 A1 1/2008 Flohr et al.
2010/0128844 A1* 5/2010 Thomsen et al. ............... 378/53
2010/0195804 A1* 8/2010 Dafni et al. .................. 378/207

OTHER PUBLICATIONS

Certified German Priority document for German Patent Application No. 10 2010 042 388.2 (Not Yet Published).

* cited by examiner

METHOD FOR CALIBRATING A CT SYSTEM WITH AT LEAST ONE FOCUS-DETECTOR COMBINATION WITH A QUANTA-COUNTING DETECTOR

PRIORITY STATEMENT

The present application hereby claims priority under 35 U.S.C. §119 on German patent application number DE 10 2010 042 388.2 filed Oct. 13, 2010, the entire contents of which are hereby incorporated herein by reference.

FIELD

At least one embodiment of the invention generally relates to a method for calibrating a CT system with at least one focus-detector combination with a quanta-counting detector having a plurality of detector elements, with the focus-detector combination being arranged to enable it to rotate around a measurement region and a system axis arranged therein, and an X-ray bundle which possesses an X-ray energy spectrum over an energy range going out from the focus to the detector, with the aid of scanning of at least one phantom, with actual attenuation values determined thereby being compared with required attenuation values and, for a subsequent scanning of a patient, a correction of the determined attenuation values taking place and a reconstruction of CT image data with the corrected attenuation values being carried out and CT image data being output and/or further processed.

BACKGROUND

Calibration methods are generally known in conjunction with computer tomographic systems (CT systems). With these known calibration methods however detectors are calibrated in measurement ranges which do not fall into the saturation range of the detector but in ranges in which a linear behavior between radiation intensity striking the detector and a signal response is largely used as the basis. Quanta-counting detectors lie in the range of the radiation intensity used for X-ray diagnostics in CT examinations at least partly in the range of strong non-linearity however, with paralysis phenomena already occurring in the detector here.

SUMMARY

In at least one embodiment of the invention, an improved calibration method delivers satisfactory results both in the non-saturated range and also in the range in which a paralysis occurs.

Advantageous developments of the invention are the subject matter of subordinate claims.

In accordance with at least one embodiment of the inventive idea described above, the inventor thus proposes at least one embodiment of a method for calibrating a CT system with at least one focus-detector combination with a quanta-counting detector having a plurality of detector elements, with the focus-detector combination being arranged to enable it to rotate around a measurement region and a system axis arranged therein and with an X-ray bundle going out from the focus to the detector which possesses an X-ray energy spectrum across an energy range, with at least one embodiment of the inventive method featuring the following method steps:

At least one-off arrangement of the at least one phantom in the measurement region such that each measurement beam of the focus-detector combination moving once around the system axis passes at least once through an area of maximum and once through an area of minimum attenuation.

At least one-off scanning of the at least one phantom from a plurality of orbitally arranged projection angles and execution of an orbital scanning without phantom using a plurality of dose power values.

Formation of a scatter plot for each detector element between actual attenuation values and required attenuation values of beams spatially identical to each other computed from the measurement values of the quanta-counting detector, with the required attenuation values relating to a predetermined singular radiation energy, Determination of at least one transfer function between the required attenuation values and the actual attenuation values for each detector element, Scanning the patient with the at least one focus-detector combination with the quanta-counting detector and output of detector measured values, calculation of attenuation values with the detector measured values, correction of the computed attenuation values with the aid of the at least one transfer function per detector element, reconstruction of CT image data with the corrected attenuation values and output and/or further processing of the CT image data.

BRIEF DESCRIPTION OF THE DRAWINGS

The invention is explained below with reference to the example embodiments in greater detail with the aid of the figures, with only the features necessary for understanding the invention being shown. The following reference characters are used: 1: CT system; 2: First X-ray tube; 3: First detector; 4: Second X-ray tube (optional); 5: Second detector (optional); 6: Gantry housing; 7: Phantom; 8: Patient bed; 9: System axis; 10: Computer system; 11: Measurement field; 12: Scatter plot; a: Required attenuation value; A: Actual attenuation value; D1: Quanta-counting detector; D2: Integrating detector; F1, F2: Focus; P1 to P3: Phantom; $Prg_1$ to $Prg_n$: Computer programs; S1, S2: Ray bundle; $S_{P1}$, $S_{P2}$: Sinogram.

The individual figures show.

DETAILED DESCRIPTION OF THE EXAMPLE EMBODIMENTS

Figure 1:
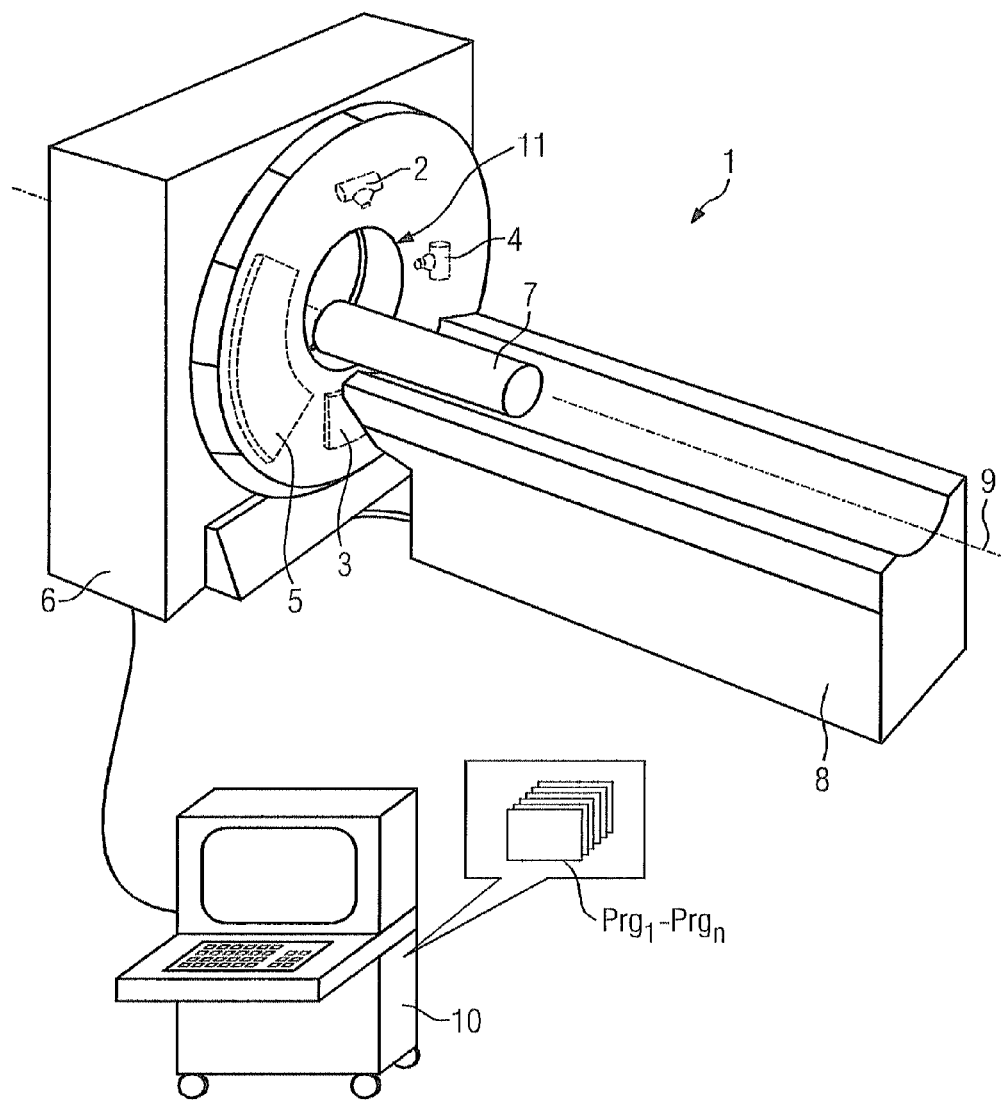
FIG. 1 a CT system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an example of a CT system 1 to be calibrated, in which a phantom 7 which is located on a movable patient bed 8 is moved along the system axis 9 through an opening in the gantry housing 6, while the gantry, not shown in any greater detail here, moves on a rotational path around the phantom 7. Located on the gantry is at least one tube detector system consisting of a first X-ray tube 2 with a quanta-counting detector 3 lying opposite it. Optionally a second tube detector system with a second X-ray tube 4 and a second detector 5 can be arranged on the same gantry. This second detector 5 can be either a second quanta-counting detector or a conventional integrating detector can be used, which can facilitate the calibration of the quanta-counting detector in accordance with the method described above. The scanning of the phantom 7 is controlled by a computer system 10, with the evaluation of the detector data and the calibration computations able to be carried out by this computer system 10.

Accordingly this computer system 10 also contains programs $Prg_1$ to $Prg_n$, with which the inventive method is carried out during operation of the CT system 1. Naturally the later scanning of patients, image reconstruction and image output or further processing of the image data can also be carried out by these programs, whereby the measurement data received by the detector system is converted into absorption data and this is corrected in accordance with a found transfer function for the purposes of calibration.

Figure 2:
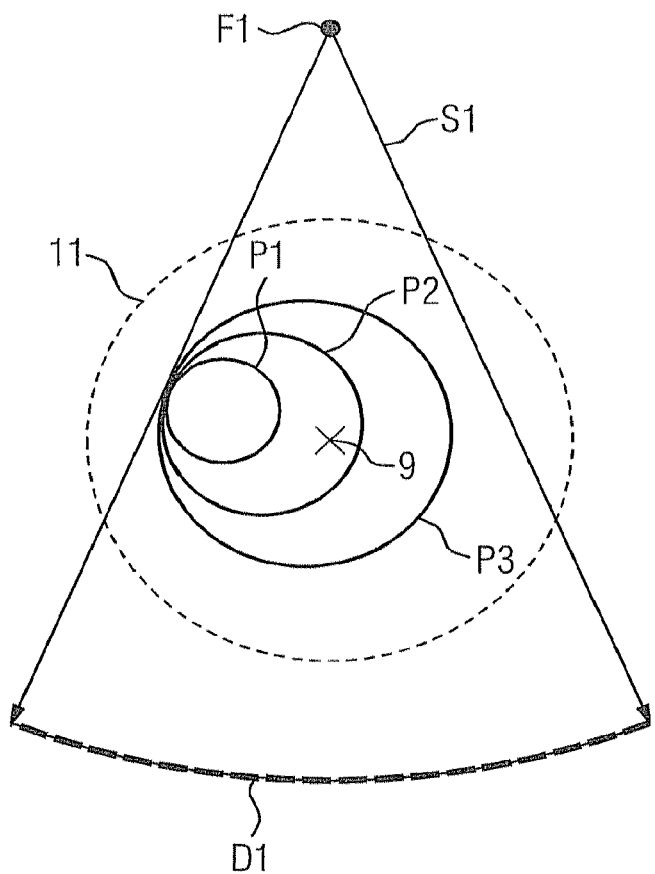
FIG. 2 a focus-detector system of the CT system with three phantom variants, FIG. 3 a sinogram of a CT system with measured actual attenuation values (on the left) and required attenuation values (on the right) for two different sizes of cylindrical phantom (top small, bottom large), FIG. 4 a scatter plot of comparative required and actual attenuation values, FIG. 5 a reconstructed CT sectional diagram of the phantom (on the left) and sectional diagram adapted to the known geometry of the phantom determined therefrom by threshold value analysis (on the right), and FIG. 6 two focus detector systems of a hybrid CT system of an integrating and a quanta-counting detector.

FIG. 2 shows a simple focus-detector system of a CT system similar to FIG. 1 with three cylindrical phantoms P1 to P3 with different diameters in cross section arranged eccentrically to the system axis 9. The focus-detector system includes a focus F1, from which a bundled ray beam or ray cone runs to the quanta-counting detector D1 arranged opposite it. The maximum usable measurement region (=FOV=field of view) 11 is indicated by dashed lines. The focus-detector system is designed to enable it to be rotated around the system axis 9, so that in rotational scanning of the phantoms P1 to P3 undertaken consecutively, sinograms are created from actual attenuation values, as are shown by way of example in FIG. 3.

Figure 3:
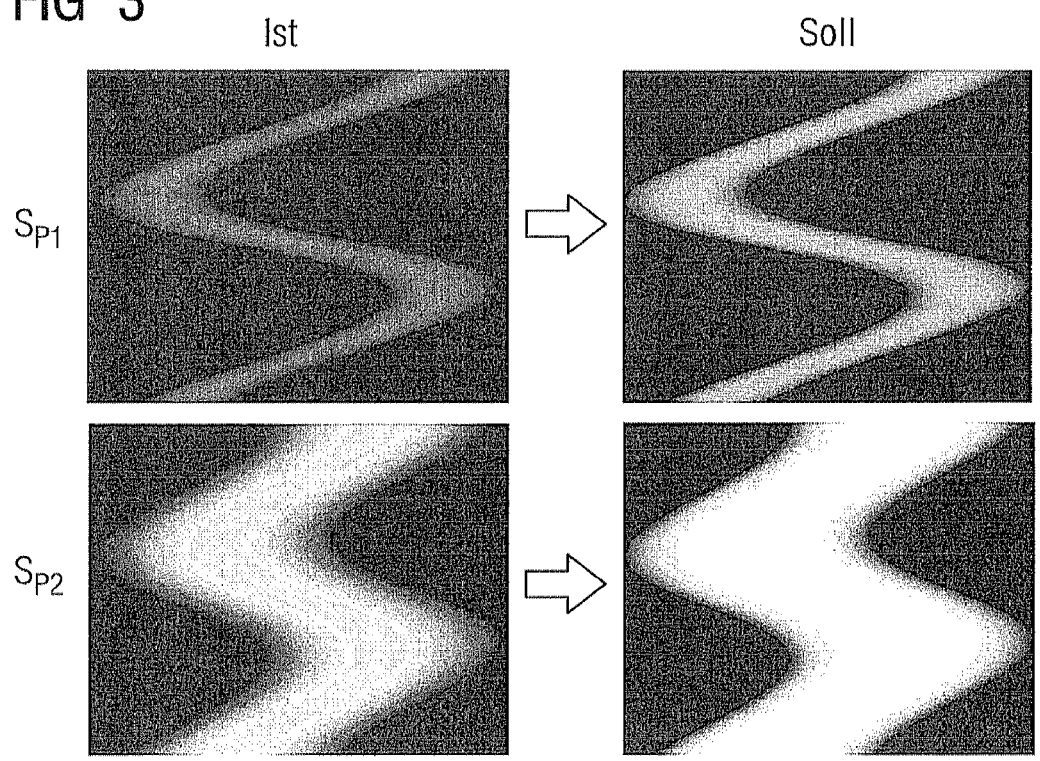

In FIG. 3 two such sinograms $S_{P1}$ and $S_{P2}$, consisting of measured actual attenuation values, are shown in the left column, which a CT system with the phantoms P1 and P2 from FIG. 2 generates. At the same time, plotted on the right alongside them are the associated sinograms with required attenuation values, which originate from theoretical computations based on known absorption values of a representative radiation energy of the phantom material. A weighted average radiation energy based on the radiation spectrum used can be used for example as representative radiation energy for measuring the sinograms $S_{P1}$ and $S_{P2}$.

Figure 4:
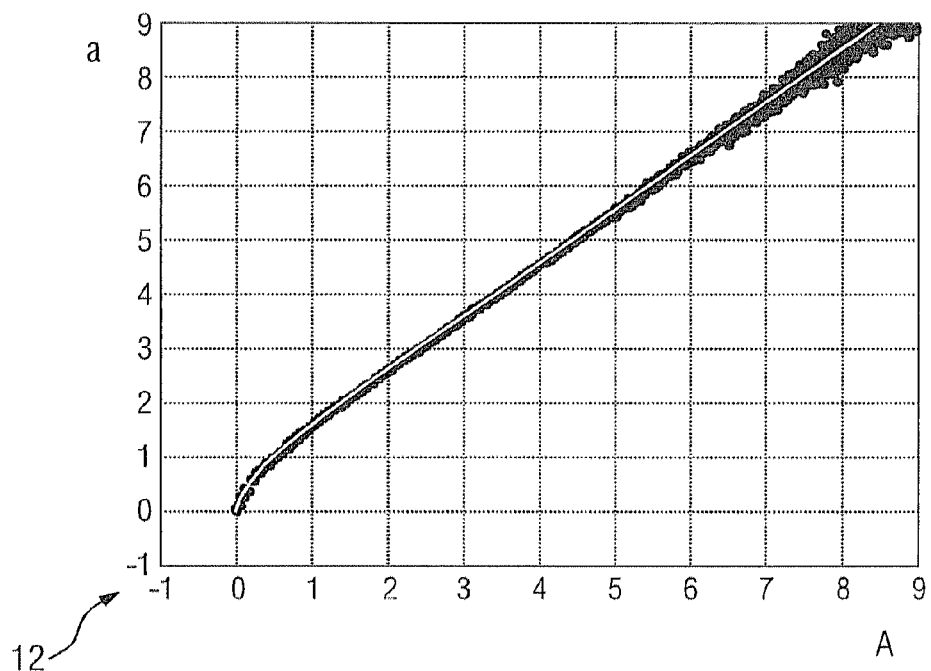

A scatter plot 12 created with the data of such required and actual attenuation values is shown in FIG. 4. Thus the monochromatic required attenuation values a are thus plotted on the ordinate against the corresponding actual attenuation values A, recorded with a given X-ray energy spectrum, on the abscissa. It is pointed out here that in the actual case of the measured values shown here the radiation intensity in the quanta-counting detector has been recorded with the aid of a so-called piggyback trigger circuit which already compensates for paralysis appearances occurring during the measurement in the high measurement range. This circuit and this measurement method is described in detail in the patent application with the file reference DE 10 2009 055 807.1, the entire contents of which are hereby incorporated herein by reference. The disclosed content of this document is to be incorporated into its entirety in the present document.

The correlation between required and actual values of the attenuation shown in FIG. 4 can now be expressed in simple equations with the aid of function adaptations, if necessary also with function adaptations segmented in relation to the radiation intensity. However the option also exists of creating a look-up table over the dimensioned area with average actual attenuation values for the required attenuation values instead of a function adaptation, if necessary interpolating intermediate values and carrying out the calibration with this look-up table.

Figure 5:
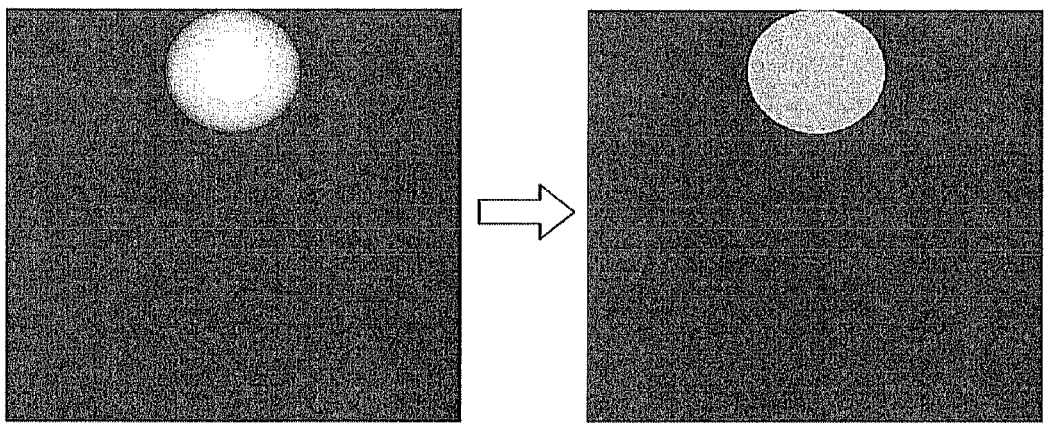

In FIG. 5 a reconstructed CT sectional image of a phantom is shown on the left and an adapted sectional image determined by threshold value analysis and adapted to the known geometry of the phantom—here a circular shape—is shown on the right. This method can be used if the position of the phantom is not to be determined by an actual measurement on the phantom in the measurement region of the CT, but this position is to be determined with the aid of a computer tomographic recording for the further theoretical computation of the required attenuation values.

Figure 6:
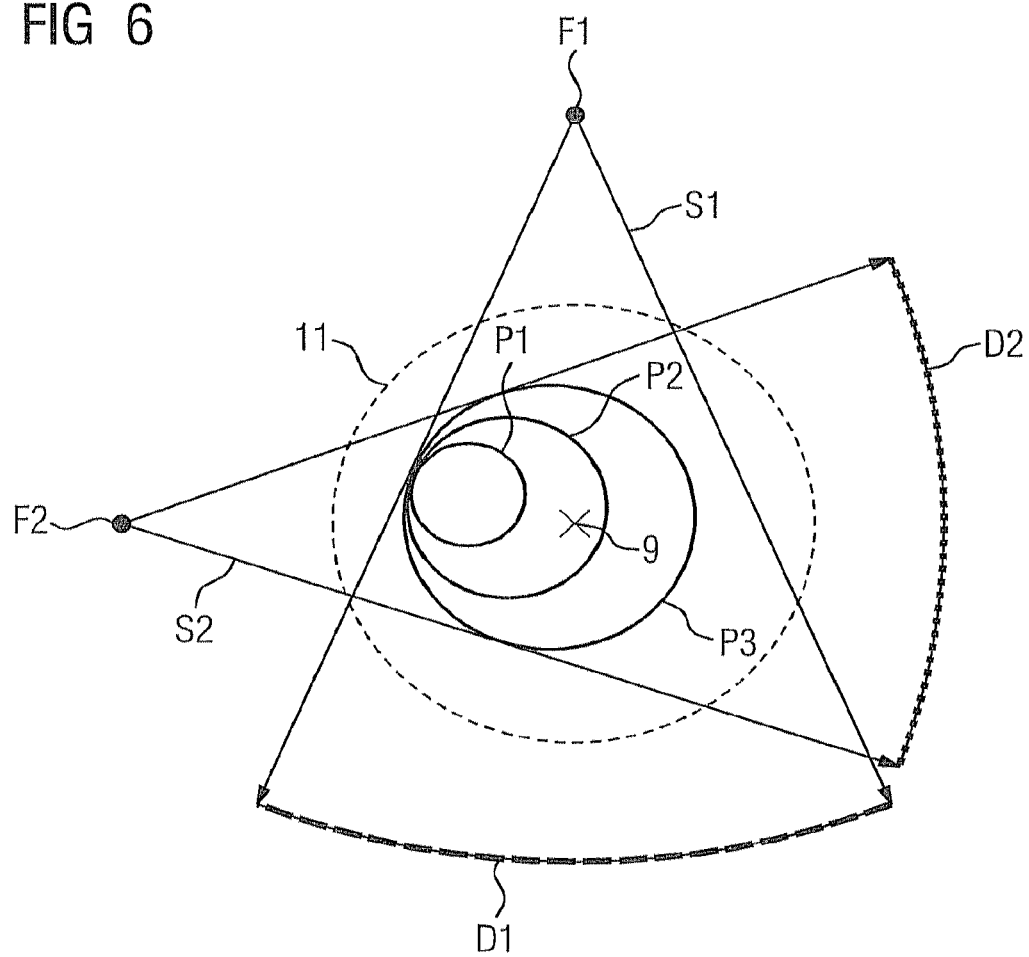

Furthermore FIG. 6 shows another version of a two-focus detector system of a hybrid CT system. The first detector system consists of the first focus F1, which casts its ray bundle S1 onto the first quanta-counting detector D1. The second focus-detector system consists of the second focus F2 which casts its ray bundle S2 onto the second integrating detector D2. Both focus-detector systems are arranged offset in this example by 90° rotationally around the system axis 9. In the present example the integrating detector also has a more tightly-meshed grid of detector elements than the quanta-counting detector, which also has a tighter beam angle.

As described above, the quanta-counting detector D1 can now be calibrated with the aid of the already calibrated integrating detector D2 and scans of the phantoms P1 to P3, whereby the different measurement grids of the two detectors as described above must be taken into consideration.

Thus a method for calibrating a CT system is described overall by embodiments of the invention, with actual attenuation values obtained from CT scans being compared with an X-ray energy spectrum with theoretical mono-energetic required attenuation values even in the paralysis area of the quanta-counting detector and a transfer function between the required attenuation values and the actual attenuation values being determined for each detector element and thereby a calibration of the measured attenuation values carried out.

The inventor has recognized the following:

Because of the high X-ray quanta flows occurring in clinical computer tomography (=CT) and a paralysis of the detector signal resulting therefrom, which leads to a non-linearity between detector signal and radiation intensity, highly complex calibration procedures will have to be implemented in future quanta-counting CT systems. The non-linearity of the detector signal, more precisely its counting rate, is subject in such cases to diverse influences such as:

The X-ray spectrum striking the detector;
The X-ray flow arriving at the detector;
The effective pixel size;
The exact value of the trigger threshold of the counter;
The characteristic and effective duration of the pulses generated by influence delivered by the detector;
And the signal-shaping characteristic of the electronics. Direct-convertor detector materials which are nowadays available as candidates for clinical CT detectors in rooms, such as CdTe, CZT etc., exhibit rather a weak homogeneity in relation to their charge collection efficiency and pulse characteristics. This means that the uncalibrated signal of such a detector is strongly inhomogeneous and mostly demands a complex individual calibration of the individual detector pixels or detector channels respectively.

Calibration methods, as are used for classical CT systems with energy-integrating detectors, can only be applied to quanta-counting systems if certain critical quanta flows are not exceeded. However these critical quanta flows are as a rule below the quanta flows occurring in clinical CT. Methods for calibration of clinical CT systems with quanta-counting detectors are not currently known.

In accordance with at least one embodiment of the invention, a method is proposed which comprises both a linearization of the detector signal and also a beam hardening correction. It goes without saying that both part aspects can also be used separately within the framework of embodiments of the invention. At least one embodiment of the inventive method described below is applied after the trigger thresholds of the counters of the individual detector pixels or detector channels respectively have been set beforehand.

In accordance with at least one embodiment of the inventive method phantoms, e.g. cylinders, ellipses, cubes etc. of a specific material, typically water, of different sizes, preferably eccentric, are positioned and scanned in the measurement region of a CT system so that each detector channel during a complete orbit covers the fullest possible range between maximum and minimum attenuation. Free air scans are also carried out. The scans of the phantoms are preferably carried out at a constant tube current (mA) for which the calibration is subsequently valid. The free air scan can be carried out both with the same and also with another mA value. The tube voltage should be selected to be identical in all scans. The essential core of the method proposed here lies in the analysis described below of the data obtained in said process and specifically in the determination of the associated required attenuation values.

In this case initially the measured intensity data of the phantoms I is converted with the aid of the intensity data from the free air scan $I_0$ for each channel separately into attenuation data A.

$$A = -\ln(I) + \ln(I_0) + c$$

with c being a freely-selectable parameter. This data A is compared with required attenuation values a, which are based on a monochromatic X-ray spectrum. The required attenuation values can be obtained in different ways, which are presented below in detail. Subsequently the following procedure is applied separately for each channel:

1. The measured attenuation data A of all projections of all phantom scans is mapped in a vector $\underline{A}$.
2. A further vector $\underline{a}$ carries the required attenuation data which corresponds to the individual components of $\underline{A}$.
3. In a scatter plot the measured values of $\underline{A}$ are plotted against the required values a. A fit or regression algorithm is used to map the data in an analytical context: $a(A, \underline{p})$, with $\underline{p}$ being the adapted parameters. Sensibly an optimized, segment-by-segment adaptation for the curve shape is carried out by means of a polynomial.

The function a(A, p) ultimately represents the calibration specification of the detector channel A→a(A, p), with the aid of which a homogenization and linearization of the detector data, including a beam hardening correction, is guaranteed.

The required attenuation values can be determined in the following different ways:

Determination of the required attenuation data as theoretical attenuation data from a sinogram fit. With the aid of the measured sinograms the distance between the phantom and the isocenter as well as the azimuth of the phantom is determined from phantom scans. The required attenuation values based on a mono-energetic X-ray spectrum are then computed analytically.

Reconstruction of the attenuation data A. Identification of the phantom by threshold value formation and segmentation into the tomographic image data with subsequent determination of the distance between the phantom and the isocenter as well as the azimuth. The required attenuation values based on a mono-energetic X-ray spectrum are computed analytically.

Reconstruction of the attenuation data A. Identification of the phantom by threshold value formation and segmentation into the tomographic image data. Modification of the image data, for example the pixels segmented as the phantom are set to 0 HU and pixels lying outside the phantom are set to −1000 HU. A forward projection of the image data is carried out, taking into consideration the exact scanner geometry, with the data from the forward projection representing the required attenuation values based on a mono-energetic X-ray spectrum.

Further versions of at least one embodiment of the method can for example be as follows:

Iterative execution of the above method to improve the position determination by way of fit or forward projection;

Multi orbits with modulation of the tube current to generate calibration specifications for diverse tube currents within a calibration pass;

Use of eccentrically arranged cylindrical phantoms or bar phantoms in static scans without rotation of the gantry;

Free air scans with modulation of the tube current instead of eccentric phantoms in rotation scans for pure linearization of the detector signal without beam hardening correction;

Segment-by-segment adaptation by means of rational functions or exponential functions;

Segment-by-segment interpolation of averaged data points by means of linear interpolation or (B) spline interpolation.

With the method described above an efficient and high-quality calibration of clinical CT systems with quanta-counting detectors as regards the linearity of the detector signal and a beam hardening correction is demonstrated, even with the highest tube currents and part paralysis of the detector signal.

Furthermore at least one embodiment of the inventive method can also be used for CT systems which are designed as dual-source CT systems and are equipped both with a conventional detector system and also with a quanta-counting detector system. If the conventional detector is already calibrated, this can be used to improve the quality of the calibration of the data from the quanta-counting detector. The basis in this case is a valid calibration of the conventional detector system as well as a geometrical transformation specification determined by known alignment methods of the data grid of the conventional detector system onto the data grid of the quanta-counting detector system.

Under these preconditions the determination of the required attenuation values described above can be optimized by the projection data of the integrating detector system fully calibrated as regards linearity and beam hardening being transformed onto the grid of the quanta-counting detector system and serving directly as required attenuation data.

Furthermore the required attenuation values for the quanta-counting detector system can be determined as theoretical attenuation data from a sinogram fit of the data of the integrating detector system, taking into account the transformation of the detector grid.

As an alternative the position of the phantom can be determined by threshold value formation and segmentation in the tomographic image data of the integrating detector system, especially by determining the distance between the phantom and the isocenter of the CT system and determining the azimuth. The required attenuation values for the quanta-counting detector system are then computed on the basis of a mono-energetic X-ray spectrum analytically with the geometry and location of the phantom thus known.

Furthermore the phantom can be localized and segmented by threshold value formation in the tomographic image data of the integrating detector system by the tomographic image data being set within the phantom to a first prespecified value, for example 0 HU, and the image data outside the phantom to a second prespecified value, for example 1000 HU. Subsequently forward projection of the image data is performed taking into consideration the exact scanner geometry related to the quanta-counting detector system. The data from the forward projection now directly represents the required attenuation values for the quanta-counting detector system based on a mono-energetic X-ray spectrum.

If the integrating detector system has a detector with a larger field of view than the quanta-counting detector system, the data of the quanta-counting detector system can be supplemented during the reconstruction with data from the integrating detector system in order to guarantee a better convergence of at least one embodiment of the above method.

At least one embodiment of the method thus describes an efficient and high-quality calibration of clinical CT systems with a quanta-counting detector, especially also the quanta-counting detector in the case of a hybrid dual-source CT system with both a quanta-counting and also a conventional detector. At least one embodiment of the inventive calibration method relates in this case both to the linearity of the detector signal and also to the beam hardening correction, even with the highest tube currents and part paralysis of the detector signal.

In accordance with at least one embodiment of the inventive idea described above, the inventor thus proposes at least one embodiment of a method for calibrating a CT system with at least one focus-detector combination with a quanta-counting detector having a plurality of detector elements, with the focus-detector combination being arranged to enable it to rotate around a measurement region and a system axis arranged therein and with an X-ray bundle going out from the focus to the detector which possesses an X-ray energy spectrum across an energy range, with at least one embodiment of the inventive method featuring the following method steps:

At least one-off arrangement of the at least one phantom in the measurement region such that each measurement beam of the focus-detector combination moving once around the system axis passes at least once through an area of maximum and once through an area of minimum attenuation.

At least one-off scanning of the at least one phantom from a plurality of orbitally arranged projection angles and execution of an orbital scanning without phantom using a plurality of dose power values.

Formation of a scatter plot for each detector element between actual attenuation values and required attenuation values of beams spatially identical to each other computed from the measurement values of the quanta-counting detector, with the required attenuation values relating to a predetermined singular radiation energy, Determination of at least one transfer function between the required attenuation values and the actual attenuation values for each detector element, Scanning the patient with the at least one focus-detector combination with the quanta-counting detector and output of detector measured values, calculation of attenuation values with the detector measured values, correction of the computed attenuation values with the aid of the at least one transfer function per detector element, reconstruction of CT image data with the corrected attenuation values and output and/or further processing of the CT image data.

It should be mentioned in this context that the plurality of the dose performance values with which the scanning of the phantom and the air measurements are carried out should preferably lie in the range of the dose power settings of the X-ray tubes actually occurring later in clinical operation and the radiation intensities becoming active later on the detector.

Preferably the transfer functions can be calculated by at least one curve adaptation of the values of the scatter plot, whereby the curve adaptation can also be carried out segment-by-segment in the scatter plot.

In an embodiment variant the required attenuation values can be calculated directly from a previously known location of the phantom in the measurement area and a previously known energy-specific coefficient of absorption of the material of the phantom, including a previously known spatial structure of the focus-detector system.

Furthermore the required attenuation values can also be determined as theoretical attenuation data from a sinogram fit, by:

The distance between the phantom and the isocenter as well as the azimuth of the phantom being determined with the aid of the measured sinograms from phantom scans, and The required attenuation values being computed analytically on the basis of the positioning thus determined and a known geometrical form of the phantom, assuming a mono-energetic X-ray spectrum.

As an alternative the option exists, by prior scanning of the phantom from at least one projection angle by at least one focus-detector combination, of determining the position of the at least one phantom. This facilitates the positioning of the phantom in the measurement region since in this case the positioning itself can be undertaken less accurately and precisely. For positioning in such cases a threshold value-based method for segmenting and identification of the at least one phantom in the tomographic image data can be used.

Furthermore the required attenuation values of the at least one phantom can also be determined by carrying out a CT scan in the reconstruction of the at least one phantom and by CT image data being determined, by all pixels/voxels with CT values above a prespecified threshold being replaced in the CT image data with a prespecified constant CT value and from this changed CT image data the required attenuation values being computed by forward projection.

It is advantageous with all of the above method variants for the phantom or phantoms of different sizes used to be arranged eccentrically to the system axis. The phantom can be embodied in the form of a bar or cylindrical or ellipsoid respectively.

It is further proposed that a number of scans of the at least one phantom be carried out with different dose power in order to generate calibration data for different dose power values within one pass.

Furthermore advantageously at least one scan of the at least one phantom with a dose power changing during a rotation of the at least one focus-detector combination and/or a number of scans without phantom with different dose power can be carried out. Also at least one scan without phantom with dose power changing during a rotation of the at least one focus-detector combination can be carried out.

It is also proposed, for determining the at least one transfer function, to carry out one of the function fits given below, especially segment-by-segment:

Spline interpolation

B spline interpolation

Fit or adaptation, preferably least-square fit of exponential function,

Fit or adaptation, least square fit of a rational function.

The calibration method described above can also be carried out in conjunction with the CT system, in which at least two focus-detector systems are used simultaneously, with at least one conventional detector being provided with integrating detector elements. In particular in this case at least the detector data of the conventional detector can also be used for determining the required attenuation values, in which case the at least one conventional detector should have already been calibrated.

It is also advantageous for the at least one focus-detector system with conventional detector and the at least one focus-detector system with quanta-counting detector to operate with an identical X-ray spectrum.

It is also advantageous for the at least one focus-detector system with conventional detector and the at least one focus-detector system with quanta-counting detector to operate during the scan with different geometrical grids (=geometrical data grids) and for calibration for the data from the grid of the conventional detector to be transferred to the grid of the quanta-counting detector or vice versa. The data can be transmitted from the geometrical grid of the conventional detector system for example by interpolation onto the grid of the quanta-counting detector.

It goes without saying that the features of the invention specified here are able to be used not only in the respective specified combination but also in other combinations or on their own, without departing from the framework of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calibrating a CT system including at least one focus-detector combination having a quanta-counting detector with a plurality of detector elements, the focus-detector combination being configured to rotate around a measurement region and a system axis of the CT system, the focus-detector combination being configured to emit an X-ray bundle having an X-ray energy spectrum over an energy range, the method comprising:

arranging at least one phantom in the measurement region such that each measurement beam of the focus-detector combination passes at least once through an area which results in a maximum attenuation and at least once through an area which results in minimum attenuation;

performing at least one first scanning of the measurement region having the arranged at least one phantom, the first scanning being carried out from a plurality of projection angles arranged around an orbit of the focus-detector combination;

performing at least one second scanning of the measurement region without the at least one phantom, the second scanning being carried out over a plurality of dosimetry power values;

forming a scatter plot for each of the plurality of detector elements and each of the dosimetry power values, the scatter plot including a comparison between actual attenuation values and theoretical attenuation values of beams spatially identical to one another, the actual attenuation values being calculated based on measured values obtained by the quanta-counting detector during the first and second scanning, each of the theoretical attenuation values being associated with one of the plurality of dosimetry power values;

determining at least one transfer function between the theoretical attenuation values and the actual attenuation values for each detector element; and calibrating the CT system based on the determined at least one transfer function.

2. The method as claimed in claim 1, wherein the transfer function is determined by at least one curve adaptation of the values of the scatter plot.

3. The method as claimed in the present claim 2, wherein the curve adaptation is carried out segment-by-segment in the scatter plot.

4. The method as claimed in claim 1, wherein the theoretical attenuation values are calculated based on a known location of the phantom in the measurement region and a known energy-specific coefficient of absorption of the material of the at least one phantom, and a known spatial structure of the focus-detector combination.

5. The method as claimed in claim 1, wherein the theoretical attenuation values are determined as theoretical attenuation data from a sinogram fit by,
determining a positioning of the at least one phantom with the aid of measured sinograms, the positioning being based on,
a distance between the at least one phantom and an isocenter of the CT system, and
an azimuth of the phantom from phantom scans, and
analytically computing the theoretical attenuation values based on the determined positioning and a known geometrical form of the at least one phantom.

6. The method as claimed in claim 1, further comprising:
determining a position of the at least one phantom from a prior scanning of the at least one phantom from at least one projection angle, the prior scanning occurring before the first and second scanning.

7. The method as claimed in claim 1, further comprising:
determining positioning information of the at least one phantom using a threshold value-based method, wherein the theoretical attenuation values are calculated based on the determined position information.

8. The method as claimed in claim 1, wherein the theoretical attenuation values of the at least one phantom are determined by a CT scan and the reconstruction of the at least one phantom being carried out and CT image data being determined, in the CT image data all pixels/voxels with CT values over a predetermined threshold being replaced by a constant CT value and from this changed CT image data the required attenuation values being computed by forwards projection.

9. The method as claimed in claim 1, wherein the at least one phantom is arranged eccentrically to the system axis.

10. The method as claimed in claim 1, wherein the at least one phantom includes a bar-shaped phantom.

11. The method as claimed in claim 1, wherein the at least one phantom includes a cylindrical phantom.

12. The method as claimed in claim 1, wherein the first scanning includes a number of scans carried out at different dosimetry power values.

13. The method as claimed in claim 1, wherein the first scanning is carried out with a dosimetry power which changes during a rotation of the at least one focus-detector combination.

14. The method as claimed in claim 1, wherein the second scanning includes a number of scans carried out with different dosimetry power values.

15. The method as claimed in claim 1, wherein the plurality of dosimetry power values change during a rotation of the at least one focus-detector combination.

16. The method as claimed in claim 1, wherein the determining at least one transfer function includes carrying out at least one of,
Spline interpolation,
B-spline interpolation,
Least-square fit of an exponential function, and
Least-square fit of a rational function.

17. The method as claimed in claim 1, wherein the at least one focus-detector combination includes two focus-detector combinations being used at the same time, one of the two focus-detector combinations having at least one conventional detector with integrating detector elements, the other of the two focus-detector combinations having the quanta-counting detector.

18. The method as claimed in claim 17, wherein at least detected data of the conventional detector is used for determining the theoretical attenuation values.

19. The method as claimed in claim 17, wherein the at least one conventional detector is already calibrated.

20. The method as claimed in claim 17, wherein the two at least one focus-detector combinations operate with an identical X-ray spectrum.

21. The method as claimed in claim 17, wherein the two focus-detector combinations operate, during the first and second scanning, with different geometrical grids and calibration data from the geometrical grid of the conventional detector is transferred to the geometrical grid of the quanta-counting detector.

22. The method as claimed in the present claim 21, wherein the data from the geometrical grid of the conventional detector system is transferred by interpolation to the geometrical grid of the quanta-counting detector.

23. A tangible non-transitory computer readable medium including program segments for, when executed on a computer device, causing the computer device to implement the method of claim 1.

24. A tangible non-transitory computer readable medium including program segments for, when executed on a computer device, causing the computer device to implement the method of claim 17.

* * * * *